(12) United States Patent
May et al.

(10) Patent No.: US 6,586,201 B1
(45) Date of Patent: Jul. 1, 2003

(54) METHOD OF CHROMATOGRAPHIC ISOLATION FOR NON-GLYCERIDE COMPONENTS

(76) Inventors: Choo Yuen May, 6, Persiaran Institusi, Bandar Baru Bangi, Kajang, Selangor (MY), 43000; Ma Ah Ngan, 6, Persiaran Institusi, Bandar Baru Bangi, Kajang, Selangor (MY), 43000; Yusof Basiron, 6, Persiaran Institusi, Bandar Baru Bangi, Kajang, Selangor (MY), 43000

( * ) Notice: Subject to any disclaimer, the term of this patent is extended or adjusted under 35 U.S.C. 154(b) by 52 days.

(21) Appl. No.: 09/703,881

(22) Filed: Nov. 2, 2000

(30) Foreign Application Priority Data

Nov. 4, 1999 (MY) ...................... PI 990 4777

(51) Int. Cl.$^7$ .................. C12P 23/00; B01D 15/08
(52) U.S. Cl. .................. 435/67; 435/52; 435/41; 435/135; 435/166; 435/167; 435/155; 435/127; 435/267; 435/271; 210/606; 210/690; 210/691; 210/749
(58) Field of Search .................. 435/41, 52, 135, 435/166, 167, 67, 155, 127, 267, 271; 210/606, 690, 691, 749

(56) References Cited

U.S. PATENT DOCUMENTS

| | | | |
|---|---|---|---|
| 2,432,021 A | 12/1947 | Larner | 167/81 |
| 2,440,029 A | 4/1948 | Tabor et al. | 260/236.5 |
| 2,460,796 A | 1/1949 | Eckey | 260/410.9 |
| 2,484,040 A | 10/1949 | Lange et al. | 260/666 |
| 2,572,467 A | 10/1951 | Gebhart | 260/236.5 |
| 2,652,433 A | 9/1953 | Blaizot | 260/666 |
| 4,122,094 A | 10/1978 | Woziwodzki | 260/345.6 |
| 5,157,132 A | 10/1992 | Tan et al. | 549/413 |
| 5,190,618 A | 3/1993 | Top et al. | 203/34 |
| 5,627,289 A | 5/1997 | Jeromin et al. | 549/413 |

FOREIGN PATENT DOCUMENTS

| | | |
|---|---|---|
| EP | 1 097 985 | 5/2001 |
| EP | 1 122 250 | 8/2001 |
| GB | 0 567 682 | 2/1945 |
| GB | 0 691 924 | 5/1953 |
| GB | 1 562 794 | 11/1976 |
| GB | 2 218 989 | 11/1989 |
| JP | 2157274 | 12/1988 |

OTHER PUBLICATIONS

Choo, Y., M., et al., "Separation of Crude Palm Oil Components by Semipreparative Supercritical Fluid Chromatography," J. Amer. Oil. Chemists' Society, United States, Journal of the American Oil Chemists, vol. 73, No. 4, Apr. 1996, pp. 523–525.

AN–L Yeh et al., "Separation of Fatty Acid Esters from Cholesterol in Esterified Natural and Synthetic Mixtures by Supoercritical Carbon Dioxide," J. Amer. Oil. Chemists' Society, United States, Journal of the American Oil Chemists, vol. 68, No. 4, Apr. 1, 1999, pp. 224–229.

Lee, H., et al., "Concentration of Tocopherols from Soybean Sludge by Supercritical Carbon Dioxide," Journal of the American Oil Chemists Society, vol. 68, No. 8, 1991, pp. 571–573.

Ibanez, E. et al., "Isolation and Separation of Tocopherols from Olive By–products with Supercritical Fluids," JAOCS 77:2, pp. 187–190, 2000.

Grezgorz Galuba et al., "Separation of Tocopherols and Sterols in Soybean Oil Condensate Utilizing Supercritical Fluid Chromatography (SFC)," Chem. Anal. 42, pp. 245–248, 1997.

A. Staby et al., "Quantitative Analysis of Marine Oils by Capillary Supercritical Fluid Chromatography," Chromatographia 39:11/12, pp. 697–705, 1994.

T. Yarita et al., "Supercritical fluid chromatographic determination of tocopherols on an ODS–silica gel column," Journal of Chromatography A., 679, pp. 329–334, 1994.

*Primary Examiner*—Francisco Prats
(74) *Attorney, Agent, or Firm*—Pennie & Edmonds LLP

(57) ABSTRACT

A method of chromatographic isolation for non-glyceride components (squalenes, carotenes, vitamin E, sterols and/or the like) from a non-glyceride components-comprising compound by the steps of a. introducing the non-glyceride components-comprising compound onto a selective adsorbent to allow an adsorption of the non-glyceride components, and subsequently b. desorbing the non-glyceride components from the adsorbent, wherein the adsorption and/or desorption of the non-glyceride components is carried out under a supercritical fluid environment.

41 Claims, No Drawings

METHOD OF CHROMATOGRAPHIC ISOLATION FOR NON-GLYCERIDE COMPONENTS

FIELD OF THE INVENTION

The invention relates to a method of chromatographic isolation for non-glyceride components particularly squalenes, carotenes, vitamin E (sometimes abbreviated as Vit. E) sterols and/or the like, from crude palm oil, palm oils products and/or by-products, vegetable oils and/or the like non-glyceride components-comprising compounds.

BACKGROUND OF THE INVENTION

Crude palm oil contains about 5% of "non-glyceride components" which include carotenoids, tocols (tocopherols and tocotrienols), sterols and squalene. The carotenoids, present at 500–700 ppm and comprising mainly α and β carotenes, are important constituents with pro-vitamin A activity, possible antitumor formation properties, and other physiological activities. The tocols which are Vitamin E and also natural anti-oxidants, are present at approximately 600 to 1000 ppm in crude palm oil; the major component being the gamma-tocotrienol which has recently been found to have anti-cancer properties besides its known anti-oxidant activity. Tocotrienol has been found to lower blood cholesterol. The sterols consisting mainly of β-sitosterol, stigmasterol and campesterol, provide raw materials for steroid intermediates and drugs. β-Sitosterol also possesses hypocholesterolemic effect. Squalene is an important ingredient for cosmetics. It also shows beneficial physiological properties.

Several methods have been developed to extract these valuable compounds. In the case of the carotenoids, the known methods can be classified as follows:

(i) Extraction by saponification e.g. British Patent 567, 682; U.S. Pat. Nos. 2,460,796; 2,440,029; 2,572,467; 2,652,433.

(ii) Iodine method (iii) Urea process (iv) Extraction using Fuller's earth or activated carbon, e.g. British Patent 691,924; British Patent 1,562,794; U.S. Pat. No. 2,484,040.

(v) Extraction by selective solvents e.g. U.S. Pat. No. 2,432,021.

(vi) Molecular Distillation.

In the saponification method (i) the oil is saponified to give soap, glycerol and a non-saponifiable fraction containing carotenes.

In the iodine method (ii), the iodine is added to a solution of palm oil in petroleum ether, an insoluble precipitate of carotene di-iodide is formed. The iodo-compound when treated with sodium thiosulphate however yields iso-carotene or dehydro-carotene which has no biological activity.

With the urea method (iii), the triglycerides are broken down to fatty acids and methyl esters which then form insoluble compounds with urea and thiourea, leaving the carotenoids in the remaining liquid.

Extraction of carotenes using adsorbents has been carried out using Fuller's earth and activated carbon (method iv). However, the extraction of the carotenes from the earth gives oxidised or isomerised products of carotenes. Carotene is concentrated six times in the extract.

Extraction of carotenes by selective solvents (method v) has been carried out using propane or furfural. The carotene is concentrated (three times that of the original oil) in the furfural phase.

By method (vi) carotenes can also be obtained by molecular distillation ($10^{-3}$–$10^{-4}$ mm Hg). Fractions collected at 230° C. have a carotene content of about five times that of the original oil.

To-date, there has not been any method which discloses the use of supercritical fluid in the adsorption/desorption chromatography isolation/separation of the non-glyceride components (i.e. carotenoids, tocols, sterols and squalene) from plant source such as CPO (crude palm oil), palm oil products and/or by-products, vegetable oils and fats and/or the like non-glyceride components-comprising compounds.

All known method previously disclosed in the adsorption/desorption cromatographic separation solely involve the use of solvents (which are costly and hazardous). Thus, there is a need to provide a separation and/or an isolation process, which avoids or discourages the sole use of solvents and consequently rendering it "non-hazardous" for recovering these non-glyceride components.

SUMMARY OF THE INVENTION

In accordance with the present invention, there is provided a method of chromatographic isolation for non-glyceride components (carotenes, vitamin E [sometimes abbreviated as Vit. E], sterols, squalene) from natural oils and fats, wherein the method comprises the use of supercritical fluid (such as SC-$CO_2$) in combination with adsorbents (such as silica gel or C18 reverse phase silica gel). The present invention may be subjected directly and/or indirectly to (a) crude vegetable oil esters (via catalytic alcoholic esterification/transesterification of vegetable oils) or (b) concentrate (through removal of the bulk of the esters from (a) via vacuum distillation including molecular distillation) or (c) the unsaponifiable matters of the concentrate in (b) (through saponification process)

High concentration of carotenes, vitamin E, sterols and squalene can be obtained by monitoring supercritical fluid process conditions such as temperature between 30° C.–100° C., pressure from 50 kg/cm$^2$ to 600 kg/cm$^2$, with and without an to entrainer (co-solvent such as alcohols).

A main advantage of the invention lies in the use of liquified gas at supercritical conditions, hence avoiding or reducing the prior requirements for hazardous solvents.

DETAILED DESCRIPTION OF THE INVENTION

According to the present invention there is provided a method of chromatographic isolation for "minor non-glyceride components" (including carotenoids, tocols, sterols and squalene) from CPO (crude palm oil), palm oil products and/or by-products, vegetable oil and/.or the like non-glyceride components-comprising compounds, said method comprising the following steps for three different routes as described below:

Route (a)

(i) Esterifying the free fatty acid component of the non-glyceride components-comprising compounds with one or more monohydric alcohols to form an esterified compound with a very low free fatty acid content;

(ii) Trans-esterifying the glyceride components with one or more monohydirc alcohols to convert into monoesters;

(iii) Introducing the non-glyceride components-comprising compounds (i.e. esters from steps (i) and (ii) above) to allow the adsorption of non-glyceride components (carotenoids, tocols, sterols and squalene) onto a selective adsorbent; and subsequently (iv) Desorbing the non-glyceride components from the adsorbent, wherein the adsorption/desorption of the non-glyceride components in steps (iii)–(iv) is carried out under a supercritical fluid environment.

Route (b)

(i) Esterifying the free fatty acid components of the non-glyceride components-comprising compounds with one or more monohydric alcohols to form an esterified compound with a very low free fatty acid content;

(ii) Trans-esterifying the glyceride components with one or more monohydirc alcohols to convert into monoesters;

(iii) Removing bulk of the esters in step (i) and (ii) by vacuum distillation including molecular distillation to yield carotene concentrate of 1–8%;

(iv) Introducing the non-glyceride components-comprsing compounds (i.e. the carotene concentrate from step (iii) above) to allow the adsorption of non-glyceride components (carotenoids, tocols, sterols and squalene) onto a selective adsorbent; and subsequently (v) Desorbing the non-glyceride components from the adsorbent, wherein the adsorption/desortion of the non-glyceride components in steps (iv)–(v) is carried out under a supercritical fluid environment.

Route (c)

(i) Esterfying the free fatty acid component of the non-glyceride components-comprising compounds with one or more monohydirc alcohols to form an esterifed compound with a very low free fatty acid content;

(ii) Trans-esterdifying the glyceride components with one or more monohydric alcohols to convert into monoesters;

(iii) Removing bulk of the esters in step (i) and (ii) by vacuum distillation including molecular distillation to yield carotene concentrate of 1–8%.

(iv) Saponifying the carotene concentrate in step (iii) to yield unsaponifiable matters;

(v) Introducing the non-glyceride components-comprising compounds to allow the adsorption of non-glyceride components (carotenoids, tocols, sterols and squalene) onto a selective adsorbent; and subsequently (vi) Desorbing the non-glyceride components from the adsorbent, wherein the adsorption/desorption of the non-glyceride components in steps (v)–(vi) is carried out under a supercritical fluid environment.

Preferably, the esterification of step (i) above is carried out employing (a) a solid alkali metal bisulphate or (b) a sulphate acid strongly-acidic ion-exchange resin.

Preferably, the transesterification of step (ii) is carried out employing a basic catalyst.

Alternatively, both the esterification and transesterification are carried out using an enzyme; for example candida rugosa and lipase. 1 to 20% by weight of catalyst may be employed depending upon the weight of the free fatty carboxylic to acid moiety present in the non-glyceride components-comprising compounds.

Preferably, the monohydric alcohols used in the esterification of step (i) or transesterification of step (ii) comprise one or more $C_1$ to $C_8$ alcohols, most preferably methanol.

Preferably, the selective adsorbent for the adsorption of the non-glyceride components comprise silica gel and/or C18 reverse phase silica gel. The adsorbents may be subjected to adsorption of the non-glyceride components present within any one of the following;

(i) the esterified palm oil; or (ii) the carotene concentrate (1–8%) wherein bulk of the esters have been removed through vacuum distillation or molecular distillation (short path distillation); or (iii) the unsaponifiable materials by saponifying the carotene concentrate of (ii).

The solvents employed for the present method comprises;

(i) Supercritical fluid, e.g. $SC\text{-}CO_2$ (100%), and/or (ii) Supercritical fluid (e.g. $SC\text{-}CO_2$) in combination with an entrainer (solvent such as alcohol)

Carotene, tocols, sterols and squalene can be isolated with >50% purity in a single run by varying pressure from 50 kg/cm$^2$–600 kg/cm$^2$ at temperatures 30° C.–100° C.

It shall therefore be illustrated, by means of the following examples, that supercritical fluid, applied to solid adsorbents such as silica gel and/or C18 reverse phase silica gel, provides a very satisfactory means for isolating non-glyceride components (including carotenoids, tocols, sterols and squalene) from CPO (crude palm oil), palm oil products and/or by-products, vegetable oil and/or the like non-glyceride components-comprising compounds.

EXAMPLE 1

Crude palm oil methyl esters containing "minor" non-glyceride components (including carotenes, vitamin E, squalene and sterols), derived from alcoholic esterification/transesterification of crude palm oil with alkali bisulphate or sulphonated ion exchange resin (for esterification) and with 0.3–2% based catalyst and methanol was passed through molecular distillation at a temperature of 90° C.–180° C. and pressure of less than 100 mTorr to give a carotene concentrate of 1–8%. The carotene concentrate was subjected to saponification process to obtain unsaponifiable matters containing carotenes, vitamin E, sterols and squalene.

A typical sample of the unsaponifiable matter of palm carotene concentrate is (0.0368 g) containing carotenes (21.6%), vitamin E (2.7%), sterols (56.5%) and squalene (8.2%) was dissolved in an organic solvent, such as dichloromethane (2 ml) and loaded onto a column (silica gel, with internal diameter 20 mm and length: 250 mm). The sample mixture was eluted using a mixture of supercritical carbon dioxide (3.0 ml, 98.4%) and entrainer, ethanol (0.05 ml, 1.6%) with a flowrate of 3.05 ml/min. The pressure of the supercritical fluid chromatography system was monitored from P=100 kg/cm$^2$ to 300 kg/cm$^2$ in 9 hours, keeping temperature constant at 80° C. Various fractions at different time intervals were collected and results are shown in Table 1. Squalene was collected at Pressure 100–180 kg/cm$^2$, Carotene at P=180–220 kg/cm$^2$; Vitamin E at P=220–280 kg/cm$^2$ and sterols at >280 kg/cm$^2$. Total carotenes, vitamin E, sterols and squalene collected in each fraction was determined by UV-visible spectrophotometer at 446 nm, HPLC (fluorescent detector, excitation 323 nm, and emission 296 nm), and GC (for sterols and squalene) respectively.

EXAMPLE 2

The procedure of example 1 was repeated except that the palm carotene concentrate (4% concentration) was used instead of unsaponifiable matters of the concentrate to recover carotenes, vitamin E, sterols and squalene separately in different fractions. Results are shown in Table 2.

EXAMPLE 3

The procedure of Example 1 was repeated except that crude palm oil methyl esters were used directly to load onto supercritical fluid chromatography to recover carotenes, vitamin E, sterols and squalene separately in different fractions. The results are shown in Table 3.

EXAMPLE 4

The procedure of Example 1 using unsaponifiable matters of the carotene concentrate was repeated except that only 100% SC-$CO_2$ (without entrainer) was used for adsorbing/ desorbing carotenes, vitamin E, sterols and squalene. Results are shown in Table 4.

EXAMPLE 5

The procedure of Example 2 using palm carotene concentrate (4% concentration) was repeated except that only 100% SC-$CO_2$ (without entrainer) was used for adsorbing/ desorbing carotenes, vitamin E, sterols and squalene. Results are shown in Table 5.

EXAMPLE 6

The procedure of Example 3 using crude palm oil methyl esters was repeated except that 100% of SC-$CO_2$ (without entrainer) was used. Results are shown in Table 6.

EXAMPLE 7

The procedure of Example 1 using unsaponifiable matters of the carotene concentrate was repeated except that the adsorbent used was C18 reverse phase silica gel instead of silica gel. Results are shown in Table 7.

EXAMPLE 8

The procedure of Example 2 using palm carotene concentrate (4% concentration) was repeated except that the adsorbent used was C18 reverse phase silica gel instead of silica gel. Results are shown in Table 8.

EXAMPLE 9

The procedure of example 3 was repeated except that crude palm oil methyl esters were used directly to load onto supercritical fluid chromatography with C18 reverse phase silica gel to recover carotenes, vitamin E, sterols and squalene. Results are shown in Table 9.

EXAMPLE 10

The procedure of example 7 using unsaponifiable matters of the carotene concentrate was repeated except that only 100% SC-$CO_2$ (without entrainer) was used for adsorbing/ describing carotenes, vitamin E, sterols and squalene onto C18 reverse phase silica gel adsorbent. Results are shown in Table 10.

EXAMPLE 11

The procedure of example 8 using palm carotene concentrate (4% concentration) was repeated except that only 100% SC-$CO_2$ (without entrainer) was used for adsorbing/ desorbing carotenes, vitamin E, sterols and squalene onto C18 reverse phase silica gel adsorbent. Results are shown in Table 11.

EXAMPLE 12

The procedure of example 9 was repeated except that crude palm oil methyl esters (instead of concentrate), 100% SC-$CO_2$ (without entrainer) and C18 reverse phase silica gel (instead of silica gel) were used. Results are shown in Table 12.

EXAMPLE 13

The procedure of Example 1, 2 and 3 were repeated except that other palm oil products such as neutralized palm oil, crude palm olein, crude palm stearin, palm fibre oil and palm fatty acid distillate were used. The results are shown in Table 13. Squalene was collected at pressure 100–180 kg/$cm^2$; carotene at P=180–220 kg/$cm^2$; vitamin E at P=220–280 kg/$cm^2$ and sterols at P>280 kg/$cm^2$.

EXAMPLE 14

The procedure of Example 1, 2 and 3 were repeated except other vegetable oils such as soybean, canola, rapeseed, coconut, sunflower seed, corn oil, olive oil were used. The results are tabulated in Table 14. Squalene was collected at pressure 100–180 kg/$cm^2$; carotene at P=180–220 kg/$cm^2$ (if any); vitamin E at P=220 280 kg/$cm^2$ and sterols at P>280 kg/$cm^2$.

EXAMPLE 15

The procedure of Examples 7, 8, and 9 using the same starting materials as described therein were repeated and the results are presented in Table 15. Some variations to the operating conditions are also presented in Table 15 .

EXAMPLE 16

Isolation of Palm Vitamin E Isomers

Vitamin E concentrate (0.01 g; concentration: ~50%) was dissolved in organic solvent, such as dichloromethane or ethanol and loaded onto a column (silica gel, with internal diameter 20 mm and length 250 mm). The Vitamin E concentrate mixture was eluted using a mixture of supercritical carbon dioxide (5 ml, 95.2%) and an entrainer, ethanol (0.25 ml, 4.8%) with a flowrate of 5.25 ml/min. The pressure of the supercritical fluid chromatography system was kept constant right through the run at P=180 kg/$cm^2$, keeping temperature constant at 70° C. The four vitamin E isomers were collected at different time interval and are shown in Table 16. The presence and concentration of Vitamin E isomer were confirmed by HPLC as in Example 1.

EXAMPLE 17

Isolation of Carotenes, Vitamin E, Sterols and Squalene (Fixed Pressure and Temperature)

The procedure of Example 16 was repeated except the unsaponifiable matter of palm carotene concentrate (0.01 g) containing carotenes (21.6%), Vit E (2.7%), sterols (56.5%) and squalene (8.2%) was used. Carotenes, Vit E, sterols and squalene were separated into different fractions and the results are shown in Table 17. The difference between Example 17 and that of Example 1 is that carotenes, Vit E, sterols and squalene can be isolated at fixed temperature (70° C.) and pressure (180 kg/$cm^2$).

EXAMPLE 18

The procedures of Examples 16 and 17 were repeated. Unsaponifiable matter of palm carotene/Vit E concentrate (0.01 g) was used and loaded onto a column (silica gel, with internal diameter 20 mm and length 200 mm). The results are shown in Table 18. Carotenes, Vit E., sterols and squalene were isolated in different fractions.

EXAMPLE 19

The procedures of Examples 16, 17 and 18 were repeated except the temperature: 40° C., pressure: 160 kg/cm$^2$ and SC-CO$_2$: ethanol (v/v=93.8%:6.2%). Unsaponifiable matter of palm carotene/vit. E concentrate (0.005 g) was used and loaded onto a column (silica gel, with internal diameter: 4.6 mm and length: 250 mm). Carotenes, Vit. E, sterols and squalene were isolated in different fractions and results are presented in Table 19.

TABLE 1

Unsaponifiable Matters (with entrainer)

| Fractions | Time (min) | Pressure (kg/cm$^2$) | Squalene (%) | Carotenes (%) | Vitamin E (%) | Sterols (%) |
|---|---|---|---|---|---|---|
| SM | — | — | 8.2 | 21.6 | 7.7 | 59.5 |
| F1 | 0–135 | 100 | 86 | — | — | — |
| F2 | 135–195 | 180 | 9.4 | 83.4 | — | — |
| F3 | 195–240 | 220 | — | 9.2 | 60.1 | — |
| F4 | 240–260 | 250 | — | 4.4 | 20.2 | — |
| F5 | 260–300 | 250 | — | 1.5 | 11.1 | — |
| F6 | 300–360 | 280 | — | 0.8 | 8.8 | 5.0 |
| F7 | 360–500 | 280 | — | — | — | 95.5 |

SM: Starting Materials

TABLE 2

Carotene Concentrate (with entrainer)

| Fractions | Time (min) | Pressure (kg/cm$^2$) | Squalene (%) | Carotenes (%) | Vitamin E (%) | Sterols (%) |
|---|---|---|---|---|---|---|
| SM | — | — | 9.8 | 4.1 | 2.3 | 5.3 |
| F1 | 0–135 | 100 | 92 | — | — | — |
| F2 | 135–195 | 180 | 4.8 | 70.6 | — | — |
| F3 | 195–240 | 220 | — | 8.2 | 13.8 | — |
| F4 | 240–260 | 250 | — | 3.1 | 57.3 | — |
| F5 | 260–300 | 250 | — | 3.2 | 22.5 | — |
| F6 | 300–360 | 280 | — | 1.4 | 6.6 | 2.4 |
| F7 | 360–500 | 280 | — | — | — | 96.6 |

SM: Starting Materials

TABLE 3

Crude Palm Oil Methyl Esters (with entrainer)

| Fractions | Time (min) | Pressure (kg/cm$^2$) | Squalene (%) | Carotenes (%) | Vitamin E (%) | Sterols (%) |
|---|---|---|---|---|---|---|
| SM | — | — | 0.03 | 0.06 | 0.06 | 0.04 |
| F1 | 0–135 | 100 | 3.6 | — | — | — |
| F2 | 135–195 | 180 | — | 10.2 | — | — |
| F3 | 195–240 | 220 | — | 3.2 | 1.2 | — |
| F4 | 240–260 | 250 | — | 1.2 | 12.6 | — |
| F5 | 260–300 | 250 | — | 12.0 | 10.8 | — |
| F6 | 300–360 | 280 | — | — | 2.8 | 0.8 |
| F7 | 360–500 | 280 | — | — | — | 3.6 |

SM: Starting Materials

TABLE 4

Unsaponifiable matters (without entrainer)

| Fractions | Time (min) | Pressure (kg/cm$^2$) | Squalene (%) | Carotenes (%) | Vitamin E (%) | Sterols (%) |
|---|---|---|---|---|---|---|
| SM | — | — | 8.2 | 21.6 | 7.7 | 59.5 |
| F1 | 0–100 | 100 | 36 | — | — | — |
| F2 | 100–160 | 180 | 88 | 2 | — | — |
| F3 | 160–200 | 220 | — | 81.3 | 0.8 | — |
| F4 | 200–240 | 250 | — | 11.7 | 12.7 | — |
| F5 | 240–260 | 250 | — | 6.6 | 73.6 | 0.9 |

TABLE 4-continued

Unsaponifiable matters (without entrainer)

| Fractions | Time (min) | Pressure (kg/cm²) | Squalene (%) | Carotenes (%) | Vitamin E (%) | Sterols (%) |
|---|---|---|---|---|---|---|
| F6 | 260–300 | 300 | — | — | 8.8 | 8.2 |
| F7 | 300–450 | 300 | — | — | — | 90.2 |

SM: Starting Materials

TABLE 5

Carotenes Concentrate (without entrainer)

| Fractions | Time (min) | Pressure (kg/cm²) | Squalene (%) | Carotenes (%) | Vitamin E (%) | Sterols (%) |
|---|---|---|---|---|---|---|
| SM | — | — | 9.8 | 4.1 | 2.3 | 5.3 |
| F1 | 0–135 | 100 | 24 | — | — | — |
| F2 | 135–195 | 180 | 76 | — | — | — |
| F3 | 195–240 | 220 | — | 67.8 | 18.7 | — |
| F4 | 240–260 | 250 | — | 18.9 | 58.9 | — |
| F5 | 260–300 | 250 | — | 8.7 | 20.3 | — |
| F6 | 300–360 | 280 | — | 0.2 | 6.1 | 11.4 |
| F7 | 360–500 | 280 | — | — | — | 83.3 |

SM: Starting Materials

TABLE 6

Crude Palm Oil Methyl Esters (without entrainer)

| Fractions | Time (min) | Pressure (kg/cm²) | Squalene (%) | Carotenes (%) | Vitamin E (%) | Sterols (%) |
|---|---|---|---|---|---|---|
| SM | — | — | 0.03 | 0.06 | 0.06 | 0.04 |
| F1 | 0–135 | 100 | — | — | — | — |
| F2 | 135–195 | 180 | 8.6 | — | — | — |
| F3 | 195–240 | 220 | — | 10.8 | — | — |
| F4 | 240–260 | 250 | — | 8.7 | 20.8 | — |
| F5 | 260–300 | 250 | — | 6.8 | 16.7 | — |
| F6 | 300–360 | 280 | — | — | 6.6 | 1.5 |
| F7 | 360–500 | 280 | — | — | — | 8.6 |

SM: Starting Materials

TABLE 7

Unsaponifiable matter (with entrainer)

| Fractions | Time (min) | Pressure (kg/cm²) | Compounds (%) | | | |
|---|---|---|---|---|---|---|
| | | | Squalene | Vitamin E | Carotenes | Sterols |
| Starting materials | — | — | 6.8 | 9.8 | 20.8 | 42.8 |
| F1 | 0–70 | 0–10 min — 100 kg/cm² | 83.8 | — | — | — |
| | | 10–20 min — 140 kg/cm² | | | | |
| F2 | 70–100 | 20–55 min — 160 kg/cm² | 12.3 | 8.3 | — | — |
| | | 55–65 min — 180 kg/cm² | | | | |
| | | 65–90 min — 200 kg/cm² | | | | |
| F3 | 100–140 | 90–300 min — 250 kg/cm² | — | 16 | 0.3 | — |
| F4 | 140–170 | >250 kg/cm² | — | 1.8 | 8.6 | — |
| F5 | 170–200 | >250 kg/cm² | — | 0.5 | 22.8 | — |
| F6 | 200–250 | >250 kg/cm² | — | — | 99.4 | 10.2 |
| F7 | 250–450 | >250 kg/cm² | — | — | — | 88.1 |

Temperature: 80° C.
Flowrate: 6.0/0.2 ml/min (SC—$CO_2$:ethanol)

TABLE 8

Carotene Concentrate (with entrainer:ethanol)

| Fractions | Time (min) | Pressure (kg/cm$^2$) | Compounds (%) | | | |
|---|---|---|---|---|---|---|
| | | | Squalene | Vitamin E | Carotenes | Sterols |
| Starting materials | — | — | 0.8 | 2.15 | 8.06 | 9.22 |
| F1 | 0–70 | 0–10 min — 100 kg/cm$^2$<br>10–20 min — 140 kg/cm$^2$ | 66.8 | — | — | — |
| F2 | 70–100 | 20–55 min — 160 kg/cm$^2$<br>55–65 min — 180 kg/cm$^2$<br>65–90 min — 200 kg/cm$^2$ | 7.5 | 76 | 0.2 | — |
| F3 | 100–140 | 90–300 min — 250 kg/cm$^2$ | — | 18 | 0.2 | — |
| F4 | 140–170 | >250 kg/cm$^2$ | — | 2 | 9.3 | — |
| F5 | 170–200 | >250 kg/cm$^2$ | — | 0.6 | 32.2 | — |
| F6 | 200–250 | >250 kg/cm$^2$ | — | — | 98.1 | 11 |
| F7 | 250–450 | >250 kg/cm$^2$ | — | — | — | 83 |

Temperature: 80° C.
Flowrate: 6.0/0.2 ml/min (SC—CO$_2$:ethanol)

TABLE 9

Crude Palm Oil Methyl Esters (with entrainer)

| Fractions | Time (min) | Pressure (kg/cm$^2$) | Compounds (%) | | | |
|---|---|---|---|---|---|---|
| | | | Squalene | Vitamin E | Carotenes | Sterols |
| Starting materials | — | — | 0.03 | 0.06 | 0.06 | 0.04 |
| F1 | 0–70 | 0–10 min — 100 kg/cm$^2$<br>10–20 min — 140 kg/cm$^2$ | 44.2 | — | — | — |
| F2 | 70–100 | 20–55 min — 160 kg/cm$^2$<br>55–65 min — 180 kg/cm$^2$<br>65–90 min — 200 kg/cm$^2$ | 3.3 | 58.2 | — | — |
| F3 | 100–140 | 90–300 min — 250 kg/cm$^2$ | — | 16.6 | 0.1 | — |
| F4 | 140–170 | >250 kg/cm$^2$ | — | 4.8 | — | — |
| F5 | 170–200 | >250 kg/cm$^2$ | — | 1.0 | 16.8 | — |
| F6 | 200–250 | >250 kg/cm$^2$ | — | — | 46.6 | 5.7 |
| F7 | 250–450 | >250 kg/cm$^2$ | — | — | — | 57.8 |

Temperature: 80° C.
Flowrate: 6.0/0.2 ml/min (SC—CO$_2$:ethanol)

TABLE 10

Unsaponifiable matter (without entrainer)

| Fractions | Time (min) | Pressure (kg/cm$^2$) | Compounds (%) | | | |
|---|---|---|---|---|---|---|
| | | | Squalene | Vitamin E | Carotenes | Sterols |
| Starting materials | — | — | 6.8 | 9.8 | 20.8 | 42.8 |
| F1 | 0–50 | 0–10 min — 100 kg/cm$^2$<br>10–20 min — 140 kg/cm$^2$ | 60 | — | — | — |
| F2 | 50–70 | 20–55 min — 160 kg/cm$^2$<br>55–100 min — 180 kg/cm$^2$<br>100–140 min — 200 kg/cm$^2$ | 89 | 7.6 | 0.01 | — |
| F3 | 70–90 | 140–180 min — 220 kg/cm$^2$<br>180–280 min — 240 kg/cm$^2$<br>280–300 min — 300 kg/cm$^2$ | — | 83 | 0.04 | — |
| F4 | 90–110 | 300 kg/cm$^2$ | — | 59 | 0.02 | — |
| F5 | 110–130 | 300 kg/cm$^2$ | — | 52 | 0.02 | — |
| F6 | 130–145 | 300 kg/cm$^2$ | — | 4 | 0.2 | 2.3 |
| F7 | 145–170 | 300 kg/cm$^2$ | — | 8 | 0.4 | 6.8 |
| F8 | 170–300 | 300 kg/cm$^2$ | — | — | 99.1 | 8.6 |
| F9 | 300–450 | 300 kg/cm$^2$ | — | — | — | 80.3 |

Temperature: 80° C.
Flowrate: 6.0 ml/min

TABLE 11

Carotene Concentrate (without entrainer)

| | | | Compounds (%) | | | |
|---|---|---|---|---|---|---|
| Fractions | Time (min) | Pressure (kg/cm$^2$) | Squalene | Vitamin E | Carotenes | Sterols |
| Starting materials | — | — | 0.8 | 2.15 | 8.06 | 9.22 |
| F1 | 0–50 | 0–10 min — 100 kg/cm$^2$ | 53 | — | — | — |
| | | 10–20 min — 140 kg/cm$^2$ | | | | |
| F2 | 50–70 | 20–55 min — 160 kg/cm$^2$ | 81 | 9.8 | 0.03 | — |
| | | 55–100 min — 180 kg/cm$^2$ | | | | |
| | | 100–140 min — 200 kg/cm$^2$ | | | | |
| F3 | 70–90 | 140–180 min — 220 kg/cm$^2$ | — | 72 | 0.2 | — |
| | | 180–280 min — 240 kg/cm$^2$ | | | | |
| | | 280–300 min — 300 kg/cm$^2$ | | | | |
| F4 | 90–110 | 300 kg/cm$^2$ | — | 59 | 0.08 | — |
| F5 | 110–130 | 300 kg/cm$^2$ | — | 51 | 0.03 | — |
| F6 | 130–145 | 300 kg/cm$^2$ | — | 6 | 0.8 | 8.4 |
| F7 | 145–170 | 300 kg/cm$^2$ | — | 10 | 1.7 | 7.6 |
| F8 | 170–300 | 300 kg/cm$^2$ | — | — | 98.3 | 2.7 |
| F9 | 300–450 | 300 kg/cm$^2$ | — | — | — | 70.3 |

Temperature: 80° C.
Flowrate: 6.0 ml/min

TABLE 12

Crude Palm Oil Methyl Esters (without entrainer)

| | | | Compounds (%) | | | |
|---|---|---|---|---|---|---|
| Fractions | Time (min) | Pressure (kg/cm$^2$) | Squalene | Vitamin E | Carotenes | Sterols |
| Starting materials | — | — | 0.03 | 0.06 | 0.06 | 0.04 |
| F1 | 0–50 | 0–10 min — 100 kg/cm$^2$ | 20 | — | — | — |
| | | 10–20 min — 140 kg/cm$^2$ | | | | |
| F2 | 50–70 | 20–55 min — 160 kg/cm$^2$ | 61 | — | — | — |
| | | 55–100 min — 180 kg/cm$^2$ | | | | |
| | | 100–140 min — 200 kg/cm$^2$ | | | | |
| F3 | 70–90 | 140–180 min — 220 kg/cm$^2$ | — | 56.7 | — | — |
| | | 180–280 min — 240 kg/cm$^2$ | | | | |
| | | 280–300 min — 300 kg/cm$^2$ | | | | |
| F4 | 90–110 | 300 kg/cm$^2$ | — | 32.2 | 0.8 | — |
| F5 | 110–130 | 300 kg/cm$^2$ | — | 31.2 | 1.6 | — |
| F6 | 130–145 | 300 kg/cm$^2$ | — | 1.3 | 1.8 | — |
| F7 | 145–170 | 300 kg/cm$^2$ | — | — | 12.2 | 3.2 |
| F8 | 170–300 | 300 kg/cm$^2$ | — | — | 57.8 | 4.6 |
| F9 | 300–450 | 300 kg/cm$^2$ | — | — | — | 58.3 |

Temperature: 80° C.
Flowrate: 6.0 ml/min

TABLE 13

(Palm oil products and by-products)

| | Palm Oil Products | Compounds (%) | | | |
|---|---|---|---|---|---|
| | | Squalene | Carotene | Vitamin E | Sterols |
| 1. | CPOs | 0.012 | 0.032 | 0.042 | 0.026 |
| | ME CPOs | 28.7 | 24.4 | 18.2 | 26.7 |
| | Concentrate CPOs | 56.2 | 48.8 | 44.3 | 56.8 |
| | Unsap. matters CPOs | 76.8 | 63.3 | 60.5 | 80.1 |
| 2. | CPOo | 0.022 | 0.092 | 0.076 | 0.033 |
| | ME CPOo | 30.6 | 38.6 | 36.4 | 44.5 |
| | Concentrate CPOo | 63.1 | 78.2 | 64.3 | 79.9 |
| | Unsap. matters CPOo | 85.8 | 95.2 | 89.1 | 98.1 |
| 3. | NPO | 0.034 | 0.065 | 0.066 | 0.044 |
| | ME NPO | 32.1 | 40.4 | 41.1 | 55.4 |
| | Concentrate NPO | 65.0 | 62.5 | 60.6 | 88.2 |
| | Unsap. matters NPO | 88.1 | 81.8 | 80.7 | 96.9 |
| 4. | PFAD | 0.8 | — | 0.78 | 1.12 |
| | ME PFAD | 36.7 | — | 45.5 | 50.8 |
| | Concentrate PFAD | 73.3 | — | 79.4 | 80.6 |
| | Unsap. matters PFAD | 92.6 | — | 88.7 | 91.3 |
| 5. | Residual fibre oil | 0.056 | 0.52 | 0.23 | 0.48 |
| | ME R fibre oil | 30.2 | 38.9 | 38.8 | 57.7 |
| | Concentrate R fibre oil | 76.3 | 60.1 | 58.6 | 78.8 |
| | Unsap. matters R fibre oil | 90.7 | 88.3 | 82.1 | 93.3 |

CPOs crude palm stearin
CPOo crude palm olein
NPO neutralised palm oil
PFAD palm fatty acid distillate
R residual
ME methyl esters

TABLE 14

Vegetable oils

| | | Compounds (%) | | |
|---|---|---|---|---|
| | Vegetable Oils | Squalene | Vitamin E | Sterols |
| 1. | Soyabean Oil (SO) | — | 0.116 | 0.320 |
| | MESO | | 27.7 | 32.2 |
| | Concentrate SO | | 52.9 | 60.7 |
| | Unsap. matter SO | | 72.8 | 90.1 |
| 2. | Sunflower seed (SU) | — | 0.064 | 0.362 |
| | ME SU | | 20.1 | 33.3 |
| | Concentrate SU | | 50.3 | 61.8 |
| | Unsap. matter SU | | 63.9 | 91.5 |
| 3. | Rapeseed oil (Ra) | — | 0.027 | 0.582 |
| | ME Ra | | 21.0 | 35.7 |
| | Concentrate Ra | | 43.7 | 65.4 |
| | Unsap. matter Ra | | 58.5 | 89.5 |
| 4. | Rice bran (Ri) | — | 0.098 | 1.52 |
| | ME Ri | | 21.6 | 46.3 |
| | Concentrate Ri | | 48.2 | 68.2 |
| | Unsap. matter Ri | | 65.8 | 96.1 |
| 5. | Olive oil (OL) | 0.688 | 0.01 | 0.11 |
| | ME OL | 26.3 | 16.6 | 32.1 |
| | Concentrate OL | 62.0 | 38.8 | 60.6 |
| | Unsap. matter OL | 89.6 | 58.1 | 88.6 |
| 6. | Corn Oil | — | 0.060 | 1.02 |
| | ME corn oil | | 21.2 | 44.4 |
| | Concentrate corn oil | | 41.8 | 65.8 |
| | Unsap. matter corn oil | | 60.5 | 92.0 |
| 7. | Coconut oil | — | — | 0.10 |
| | ME coconut oil | | | 31.3 |
| | Concentrate coconut oil | | | 58.5 |
| | Unsap. matter coconut oil | | | 84.7 |

TABLE 15

| Fractions | Collctn time (min) | Eluent $CO_2$/ent. ml/min | Cpds % | (A) Unsap. matters | (B) Carotene Conc. | (C) Crude Palm Oil Methyl Esters |
|---|---|---|---|---|---|---|
| 1 | 0–90 | 6 ml/0 ml | Methyl esters | — | 20 | 99.9 |
| | | | Squalene | 95 | 80 | 0.02 |
| 2 | 90–190 | 6 ml/0 ml & 6 ml/0.2 ml | Vit. E | 81 | 76.3 | 68.9 |
| | | | Sterols | 18.9 | 14.2 | 6.2% |
| 3 | 190–210 | 6 ml/0.2 ml & 6 ml/0.4 ml | Sterols | 80.2 | 54.2 | 26.1 |
| | | | Vit. E | 18.8 | 16.8 | 10.9 |
| 4 | 210–270 | 6 ml/1 ml | Carotenes | 96 | 82.3 | 54.7 |

Operating pressure: 180 kg/cm²

TABLE 16

Isolation of Palm Vit. E isomers (α-T, α-T3, γ-T3 and δ-T3)

| Fractions | Collection Time (min) | Vit. E α-T | Vit. E α-T3 | Vit. E γ-T3 | Vit. E δ-T3 |
|---|---|---|---|---|---|
| S/M | — | 12.7 | 11.4 | 19 | 5.8 |
| 1 | | | | | |
| 2 | 41–47 | 100 | | | |
| 3 | 47–54 | | 100 | | |
| 4 | 54–61 | | | 100 | |
| 5 | 61–77 | | | 99 | 1 |
| 6 | 77–145 | | | 33 | 97 |
| 7 | 145– | | | | | a. S/M: Starting material (Vit. E concentrate ~50%)
b. T: tocopherol
c. T3: tocotrienol TABLE 16-continued Isolation of Palm Vit. E isomers (α-T, α-T3, γ-T3 and δ-T3)

| Fractions | Collection Time (min) | Vit. E α-T | Vit. E α-T3 | Vit. E γ-T3 | Vit. E δ-T3 |
|---|---|---|---|---|---| d. Conditions: P = 180 kg/cm², T = 70° C.
e. SC—$CO_2$:ethanol = 5 ml:0.25 ml (95.2%:4.8%)

TABLE 17

Unsaponifiable matters (with entrainer)

| Fractions | Time (min) | Squalene (%) | Carotenes (%) | Vit. E (%) | Sterols (%) |
|---|---|---|---|---|---|
| S/M | — | 8.2 | 21.6 | 7.7 | 59.5 |
| F1 | 0–34 | 98.0 | | | |
| F2 | 34–41 | | 90.0 | | |
| F3 | 41–47 | | 20.0 | (α-T) 80.0 | |
| F4 | 47–54 | | | (α-T3) 100.0 | |
| F5 | 54–61 | | | (α-T3) 100.0 | |
| F6 | 61–72 | | | (γ-T3) 100.0 | |
| F7 | 72–77 | | | (γ-T3) 10.0 | 90.0 |
| F8 | 77–145 | | | (δ-T3) 100.0 | |

Conditions:
P=180 kg/cm², T=70° C.
SC-$CO_2$: ethanol=5 ml: 0.25 ml (95.2%:4.8%, v/v)

TABLE 18

Carotene and Vit. E Concentrate

| Fractions | Time (min) | Squalene (%) | Carotenes (%) | Vit. E (%) | Sterols (%) |
|---|---|---|---|---|---|
| S/M | | 8.2 | 21.6 | 48.8 | 21.3 |
| F1 | 0–7 | 96 | | | |
| F2 | 7–11 | | 90 | (α-T) 10.0 | |
| F3 | 11–13 | | 15 | (α-T) 85.0 | |
| F4 | 13–14 | | | (α-T3) 98.0 | |
| F5 | 15–20 | | | (γ-T3) 98.0 | |
| F6 | 20–25 | | | (δ-T3) 98.0 | |
| F7 | 25–40 | | | | 98 |

Silica column: 20 mm ID×200 mm length
Condition:
P=180 kg/cm², T=70° C.
SC-CO$_2$: ethanol=(95%:5%, v/v)

TABLE 19

| Fractions | Time (min) | Squalene (%) | Carotenes (%) | Vit. E (%) | Sterols (%) |
|---|---|---|---|---|---|
| S/M |  | 8.2 | 21.6 | 48.8 | 21.3 |
| 1 | 0–1.5 | 98 |  |  |  |
| 2 | 1.5–2.5 |  | 92 |  |  |
| 3 | 2.5–3.2 |  |  | (α-T) 96.0 |  |
| 4 | 3.2–3.8 |  |  | (α-T3) 98.0 |  |
| 5 | 3.8–4.2 |  |  | (γ-T3) 98.0 |  |
| 6 | 4.2–5 |  |  | (δ-T3) 98.0 |  |
| 7 | 5–8 |  |  |  | 99 |

Conditions:
P=160 kg/cm², T=40° C.
SC-CO$_2$: ethanol=3.0:0.2 (mls/min) (93.75%:6.25%, v/v)

What is claimed is:

1. A method for the chromatographic isolation of squalenes, sterols, vitamin E, and carotenes from a vegetable oil comprising free fatty acid components and glyceride components comprising:
   a. esterifying the free fatty acid components with one or more monohydric alcohols to provide an esterified composition having a fatty acid content that is less than 0.5% and transesterifying the glyceride components of the esterified composition into monoesters to form an esterified and transesterified composition;
   b. separating the squalenes, sterols, vitamin E, and carotenes from the esterified and transesterified composition by adsorbing the squalenes, sterols, vitamin E, and carotenes on a single type of adsorbent and then desorbing the squalenes, sterols, vitamin E, and carotenes from the adsorbent,
   wherein the squalenes, sterols, vitamin E, and carotenes are adsorbed and desorbed in a single run of separation, using a supercritical fluid, under isochratic conditions, at a constant temperature, and a constant flow rate.

2. The method of claim 1, wherein the desorbing is conducted at a constant pressure.

3. The method of claim 1, wherein the adsorbent is silica gel or C-18 reverse phase silica gel.

4. The method of claim 1, wherein the supercritical fluid is 100% CO$_2$.

5. The method of claim 1, wherein the supercritical fluid comprises at least 80% CO$_2$ and not more than 20% of an entrainer.

6. The method of claim 5, wherein the entrainer is an organic solvent.

7. The method of claim 6, wherein the organic solvent is an alkyl alcohol.

8. The method of claim 1, wherein the temperature is between 30° C. and 60° C. and the pressure is between 50 kg/cm² and 600 kg/cm².

9. The method of claim 2, wherein the pressure is between 75 kg/cm² and 350 kg/cm².

10. The method of claim 1, wherein esterifying the free fatty acid components of the vegetable oil is carried out by contacting the vegetable oil with a solid alkali metal bisulfate, a sulfate acid, a strongly acidic ion exchange resin catalyst, or a combination thereof and transesterifying the glyceride components is carried out by contacting the vegetable oil with a basic catalyst.

11. The method of claim 1, wherein the free fatty acid components are esterified with a C$_1$–C$_8$ alcohol, the glyceride components are transesterified with a C$_1$–C$_8$ alcohol, or the free fatty acid components are esterified with and the glyceride components are transesterified with a C$_1$–C$_8$ alcohol.

12. The method of claim 1, wherein the C$_1$–C$_8$ alcohol is methanol.

13. A method for the chromatographic isolation of squalenes, sterols, vitamin E, and carotenes from a vegetable oil comprising free fatty acid components and glyceride components comprising:
   a. esterifying the free fatty acid components with one or more monohydric alcohols to provide an esterified composition having a fatty acid content of less than 0.5% and transesterifying the glyceride components of the esterified composition with one or more monohydric alcohols to provide monoesters to form an esterified and transesterified composition;
   b. removing at least 90% of the esterified fatty acids and monoesters from the esterified and transesterified composition by vacuum distillation to provide a phytonutrient concentrate;
   c. separating the squalenes, sterols, vitamin E, and carotenes from the phytonutrient concentrate by adsorbing the squalenes, sterols, vitamin E, and carotenes on an adsorbent and then desorbing the squalenes, sterols, vitamin E, and carotenes from the adsorbent,
   wherein the squalenes, sterols, vitamin E, and carotenes are adsorbed and desorbed under a supercritical fluid environment.

14. The method of claim 13, wherein the adsorbent is silica gel or C-18 reverse phase silica gel.

15. The method of claim 13, wherein the supercritical fluid is 100% CO$_2$.

16. The method of claim 13, wherein the supercritical fluid comprises at least 80% CO$_2$ and not more than 20% of an entrainer.

17. The method of claim 16, wherein the entrainer is an organic solvent.

18. The method of claim 17, wherein the organic solvent is an alkyl alcohol.

19. The method of claim 13, wherein the temperature is between 30° C. and 60° C. and the supercritical fluid is at a pressure of between 50 kg/cm² and 600 kg/cm².

20. The method of claim 13, wherein the pressure is between 75 kg/cm² and 350 kg/cm².

21. The method of claim 13, wherein esterifying the free fatty acid components of the vegetable oil is carried out by contacting the vegetable oil with a solid alkali metal bisulfate, a sulfate acid, a strongly acidic ion exchange resin catalyst, or a combination thereof and transesterifying the glyceride components is carried out by contacting the vegetable oil with a basic catalyst.

22. The method of claim 13, wherein the free fatty acid components are esterified with a C$_1$–C$_8$ alcohol, the glyceride components are transesterified with a C$_1$–C$_8$ alcohol, or the free fatty acid components are esterified with and the glyceride components are transesterified with a C$_1$–C$_8$ alcohol.

23. The method of claim 22, wherein the C$_1$–C$_8$ alcohol is methanol.

24. The method of claim 13, further comprising saponifying the phytonutrient concentrate to provide unsaponifiable matter subsequent to step (a) and step (b) but prior to step (c).

25. A method for the chromatographic isolation of squalenes, sterols, vitamin E, and carotenes from a vegetable oil comprising free fatty acid components and glyceride components comprising:
   a. esterifying the free fatty acid components with one or more monohydric alcohols to provide an esterified composition having a fatty acid content that is less than 0.5% and transesterifying the glyceride components of the esterified composition with one or more monohydric alcohols to provide monoesters to form an esterified and transesterified composition;
   b. removing at least 90% of the esterified fatty acids and monoesters from the esterified and transesterified composition by vacuum distillation to provide a phytonutrient concentrate;
   c. separating the squalenes, sterols, vitamin E, and carotenes from the phytonutrient concentrate by adsorbing the squalenes, sterols, vitamin E, and carotenes on a single type of adsorbent and then desorbing the squalenes, sterols, vitamin E, and carotenes from the adsorbent;
   wherein the squalenes, sterols, vitamin E, and carotenes are adsorbed and desorbed in a single run of separation, using a supercritical fluid, under isochratic conditions, at a constant temperature, and a constant flow rate.

26. The method of claim 25, wherein the desorbing is conducted at a constant pressure.

27. The method of claim 25, wherein the temperature is between 30° C. and 60° C. and the pressure is between 50 kg/cm$^2$ and 600 kg/cm$^2$.

28. The method of claim 13, wherein the distillation is carried out at a temperature of between 90° C. and 180° C. and a pressure of less than 100 mTorr.

29. The method of claim 25, wherein the distillation is carried out at a temperature of between 90° C. and 180° C. and a pressure of less than 100 mTorr.

30. The method of claim 1, wherein the vegetable oils comprises crude palm oil, palm oil products, palm oil by-products, soyabean oil, sunflower seed oil, rapeseed oil, rice bran oil, olive oil, corn oil, or coconut oil.

31. The method of claim 13, wherein the vegetable oils comprises crude palm oil, palm oil products, palm oil by-products, soyabean oil, sunflower seed oil, rapeseed oil, rice bran oil, olive oil, corn oil, or coconut oil.

32. The method of claim 25, wherein the vegetable oils comprises crude palm oil, palm oil products, palm oil by-products, soyabean oil, sunflower seed oil, rapeseed oil, rice bran oil, olive oil, corn oil, or coco nut oil.

33. The method of claim 13, wherein the vacuum distillation is a molecular distillation.

34. The method of claim 25, wherein the vacuum distillation is a molecular distillation.

35. The method of claim 25, wherein the pressure is between 75 kg/cm$^2$ and 350 kg/cm$^2$.

36. The method of claim 1, wherein the vegetable oil is palm oil and further comprising separating the vitamin E into α-tocopherol, α-tocotrienol, δ-tocotrienol, and γ-tocotrienol by adsorbing the α-tocopherol, α-tocotrienol, δ-tocotrienol, and γ-tocotrienol on a single type of adsorbent and then desorbing the α-tocopherol, α-tocotrienol, δ-tocotrienol, and γ-tocotrienol from the adsorbent,
   wherein the α-tocopherol, α-tocotrienol, δ-tocotrienol, and γ-tocotrienol are adsorbed and desorbed in a single run of separation, using a supercritical fluid, under isochratic conditions, at a constant temperature, and a constant flow rate.

37. The method of claim 13, wherein the vegetable oil is palm oil and further comprising separating the vitamin E into α-tocopherol, α-tocotrienol, δ-tocotrienol, and γ-tocotrienol by adsorbing the α-tocopherol, α-tocotrienol, δ-tocotrienol, and γ-tocotrienol on a single type of adsorbent and then desorbing the α-tocopherol, α-tocotrienol, δ-tocotrienol, and γ-tocotrienol from the adsorbent,
   wherein the α-tocopherol, α-tocotrienol, δ-tocotrienol, and γ-tocotrienol are adsorbed and desorbed under a supercritical fluid environment.

38. The method of claim 25, wherein the vegetable oil is palm oil and further comprising separating the vitamin E into α-tocopherol, α-tocotrienol, δ-tocotrienol, and γ-tocotrienol by adsorbing the α-tocopherol, α-tocotrienol, δ-tocotrienol, and γ-tocotrienol on a single type of adsorbent and then desorbing the α-tocopherol, α-tocotrienol, δ-tocotrienol, and γ-tocotrienol from the adsorbent,
   wherein the α-tocopherol, α-tocotrienol, δ-tocotrienol, and γ-tocotrienol are adsorbed and desorbed in a single run of separation, using a supercritical fluid, under isochratic conditions, at a constant temperature, and a constant flow rate.

39. The method of claim 24, wherein the vegetable oil is palm oil and further comprising separating the vitamin E into α-tocopherol, α-tocotrienol, δ-tocotrienol, and γ-tocotrienol by adsorbing the α-tocopherol, α-tocotrienol, δ-tocotrienol, and γ-tocotrienol on a single type of adsorbent and then desorbing the α-tocopherol, α-tocotrienol, δ-tocotrienol, and γ-tocotrienol from the adsorbent,
   wherein the α-tocopherol, α-tocotrienol, δ-tocotrienol, and γ-tocotrienol are adsorbed and desorbed in a single run of separation, using a supercritical fluid, under isochratic conditions, at a constant temperature, and a constant flow rate.

40. The method of claim 13, wherein the temperature is between 30° C. and 100° C. and the supercritical fluid is at a pressure of between 50 kg/cm$^2$ and 600 kg/cm$^2$.

41. The method of claim 25, wherein the temperature is between 30° C. and 100° C. and the supercritical fluid is at a pressure of between 50 kg/cm$^2$ and 600 kg/cm$^2$.

* * * * *

UNITED STATES PATENT AND TRADEMARK OFFICE
CERTIFICATE OF CORRECTION

PATENT NO. : 6,586,201 B2 Page 1 of 1
DATED : July 1, 2003
INVENTOR(S) : Choo Yuen May et al.

It is certified that error appears in the above-identified patent and that said Letters Patent is hereby corrected as shown below:

<u>Column 18,</u>
Line 7, delete "claim 1" and insert -- claim 11. --.

Signed and Sealed this

Eleventh Day of April, 2006

JON W. DUDAS
*Director of the United States Patent and Trademark Office*